United States Patent [19]
Barnitz et al.

[11] Patent Number: 5,624,394
[45] Date of Patent: Apr. 29, 1997

[54] VACUUM SYSTEM AND A METHOD OF OPERATING A VACUUM SYSTEM

[75] Inventors: James C. Barnitz, Schwenksville; Joseph M. Curley, Lansdale; David C. Downey, Holland, all of Pa.

[73] Assignee: Iolab Corporation, Claremont, Calif.

[21] Appl. No.: 330,920

[22] Filed: Oct. 28, 1994

[51] Int. Cl.⁶ .................................................. A61M 31/00
[52] U.S. Cl. ............................. 604/67; 604/119; 417/28; 417/44.2; 417/44.3
[58] Field of Search ............................... 604/30, 65, 66, 604/67, 151, 27, 31, 35, 118, 119, 131, 315, 246; 128/DIG. 12, DIG. 13, 902; 417/28, 44.2, 44.3

[56] References Cited

U.S. PATENT DOCUMENTS

| | | |
|---|---|---|
| Re. 33,250 | 7/1990 | Cook . |
| 3,360,185 | 12/1967 | Woolridge . |
| 3,589,363 | 6/1971 | Banko et al. . |
| 3,599,639 | 8/1971 | Spotz . |
| 3,693,613 | 9/1972 | Kelman . |
| 3,723,030 | 3/1973 | Gelfand . |
| 3,841,799 | 10/1974 | Spinosa et al. . |
| 3,920,014 | 11/1975 | Banko . |
| 4,024,866 | 5/1977 | Wallach . |
| 4,144,644 | 3/1979 | Olsen . |
| 4,167,943 | 9/1979 | Banko . |
| 4,168,707 | 9/1979 | Douvas et al. . |
| 4,180,074 | 12/1979 | Murry et al. . |
| 4,184,510 | 1/1980 | Murry et al. . |
| 4,187,057 | 2/1980 | Xanthopoulos . |
| 4,226,590 | 10/1980 | Hofmann . |
| 4,236,880 | 12/1980 | Archibald . |
| 4,256,437 | 3/1981 | Brown . |
| 4,256,442 | 3/1981 | Lamadrid et al. . |
| 4,324,243 | 4/1982 | Helfgott et al. . |
| 4,395,258 | 7/1983 | Wang et al. . |
| 4,424,011 | 1/1984 | O'Brien et al. . |
| 4,445,826 | 5/1984 | Tarr . |
| 4,464,172 | 8/1984 | Lichtenstein . |
| 4,468,219 | 8/1984 | George et al. . |
| 4,475,904 | 10/1984 | Wang . |
| 4,479,760 | 10/1984 | Bilstad et al. . |
| 4,482,347 | 11/1984 | Borsanyi . |

(List continued on next page.)

FOREIGN PATENT DOCUMENTS

| | | |
|---|---|---|
| 0040181 | 11/1981 | European Pat. Off. . |
| 2176717 | 1/1987 | United Kingdom . |
| WO8607249 | 12/1986 | WIPO . |

OTHER PUBLICATIONS

Search report dated Jan. 26, 1996, PCT application No. PCT/US95/13592, filed Oct. 27, 1995.

Primary Examiner—Mark Bockelman
Attorney, Agent, or Firm—Loeb & Loeb LLP

[57] ABSTRACT

A vacuum system and a method of operating a vacuum system. The system comprises a vacuum line, a pump, a pump motor, a pressure adjusting assembly, a pressure sensor and a control device. The pump is connected to the vacuum line for drawing fluids therefrom, and the motor is connected to the pump to drive the pump. The pressure adjusting assembly is connected to the vacuum line for conducting fluid into that line at an adjustable rate. The pressure sensor is connected to the vacuum line to generate a pressure signal representing the pressure in the vacuum line. The control device receives the pressure signal and generates a system control signal that is used to adjust the pressure in the vacuum line. The specific manner in which the pressure in the vacuum line is adjusted depends on the value of that pressure, and in particular, whether that pressure is in a first range or a second range. If the pressure in the vacuum line is in the first range, the pressure in the vacuum line is adjusted by varying the amount of fluid conducted into that line through the pressure adjusting assembly. If the pressure in the vacuum line is within the second pressure range, the pressure in the fluid line is adjusted by varying the speed of the pump. The vacuum system is well suited for use during ophthalmic surgery to aspirate the surgical site.

7 Claims, 3 Drawing Sheets

U.S. PATENT DOCUMENTS

| | | |
|---|---|---|
| 4,493,695 | 1/1985 | Cook . |
| 4,493,698 | 1/1985 | Wang et al. . |
| 4,515,589 | 5/1985 | Austin et al. . |
| 4,526,515 | 7/1985 | DeVries . |
| 4,537,561 | 8/1985 | Xanthopoulos . |
| 4,599,055 | 7/1986 | Dykstra . |
| 4,626,248 | 12/1986 | Scheller . |
| 4,627,833 | 12/1986 | Cook . |
| 4,643,717 | 2/1987 | Cook et al. . |
| 4,650,469 | 3/1987 | Berg et al. . |
| 4,664,601 | 5/1987 | Uchida et al. . |
| 4,670,006 | 6/1987 | Sinnett et al. . |
| 4,685,902 | 8/1987 | Edwards et al. . |
| 4,706,687 | 11/1987 | Rogers . |
| 4,710,163 | 12/1987 | Butterfield ................ 604/65 |
| 4,713,051 | 12/1987 | Steppe et al. . |
| 4,714,464 | 12/1987 | Newton . |
| 4,735,558 | 4/1988 | Kienholz et al. . |
| 4,740,202 | 4/1988 | Stacey et al. . |
| 4,757,814 | 7/1988 | Wang et al. . |
| 4,758,238 | 7/1988 | Sunblom et al. . |
| 4,759,349 | 7/1988 | Betz et al. . |
| 4,770,187 | 9/1988 | Lash et al. . |
| 4,770,654 | 9/1988 | Rogers et al. . |
| 4,773,897 | 9/1988 | Scheller et al. . |
| 4,790,816 | 12/1988 | Sunblom et al. . |
| 4,798,580 | 1/1989 | DeMeo et al. . |
| 4,810,242 | 3/1989 | Sunblom et al. . |
| 4,820,265 | 4/1989 | DeSatnick et al. . |
| 4,838,281 | 6/1989 | Rogers et al. . |
| 4,838,865 | 6/1989 | Flank et al. . |
| 4,898,579 | 2/1990 | Groshong et al. . |
| 4,900,302 | 2/1990 | Newton . |
| 4,902,276 | 2/1990 | Zakko . |
| 4,904,168 | 2/1990 | Cavoto et al. . |
| 4,933,843 | 6/1990 | Scheller et al. . |
| 4,988,336 | 1/1991 | Kohn ................ 604/67 |
| 5,087,245 | 2/1992 | Doan ................ 604/67 |
| 5,125,891 | 6/1992 | Hossain et al. . |
| 5,242,404 | 9/1993 | Conley et al. ........ 604/67 X |
| 5,249,121 | 9/1993 | Baum et al. . |
| 5,328,478 | 7/1994 | McVay ................ 604/65 X |
| 5,346,470 | 9/1994 | Hobbs et al. ........ 604/30 X |
| 5,368,559 | 11/1994 | Kusmierczyk et al. . |
| 5,380,280 | 1/1995 | Peterson ................ 604/65 |

VACUUM SYSTEM AND A METHOD OF OPERATING A VACUUM SYSTEM

BACKGROUND OF THE INVENTION

This invention generally relates to vacuum systems and to methods of operating vacuum systems. More specifically, the present invention relates to such systems and methods that are particularly well suited for use in surgical procedures, especially micro surgery, to aspirate the surgical site.

Microsurgical procedures are gaining everincreasing acceptance in the surgical community for preforming precise, minimum invasive surgery for various parts of the body, and one particularly widespread microsurgical application is in the field of ophthalmology.

In this application, commonly, a hand piece having a small tool is used either to cut or to mascerate the eye tissue while an irrigation or infusion liquid is brought to the surgery site. The cut or mascerated tissue is carried away from the surgical site by a suction conduit or tube to a collection vessel such as a bag or bottle. The surgical site may be illuminated by light conducted to that site through an optical fiber.

Consoles are specifically designed for these ophthalmic procedures. These consoles are used to operate the tools and the suction and infusion lines used in the procedures, and to generate the light that is used to illuminate the surgical site. Typically, these consoles have a modular design and include a multitude of separable or removable modules, with each module being used to operate or to perform a specific task. For example, one module may be employed to operate the hand piece used to cut or mascerate the eye tissue, another module may be used to infuse and aspirate the surgical site, and a third module may be used to illuminate that site.

In these procedures, typically, an operator is able to vary the vacuum pressure used to aspirate the surgical site. With one prior art device, for example, this is done by using a diaphragm pump to draw air from a vacuum line, in combination with an adjustable bleed line to bleed air into that vacuum line. More specifically, the pump is operated at a substantially constant speed so that, in the absence of any effect from the bleed line, a substantially constant vacuum pressure would be maintained in the vacuum line. At the same time, a valve in the bleed line is operated, under the control of an operator, to bleed an adjustable amount of air into the vacuum line to vary the pressure therein. For instance, the diaphragm pump may be used to develop a pressure in the vacuum line of 500 mm. of mercury. If the operator wants to increase the pressure in that line, air is bled into the vacuum line until the desired pressure level is reached.

This prior art device is highly effective and reliable. However, the diaphragm pump is some what noisy. In addition, in order to vary the vacuum pressure in the vacuum line over the desired range, a comparatively large valve is required to regulate air flow through the bleed line. Because this valve is large, it is relatively expensive and a comparatively complicated control mechanism is needed to operate the valve.

SUMMARY OF THE INVENTION

An object of this invention is to improve vacuum systems and methods of operating vacuum systems.

Another object of this invention is to vary the pressure in a vacuum line either by varying the operation of a pump connected to the vacuum line, or by adjusting the amount of air bled into the vacuum line, depending on whether the pressure in the vacuum line is, respectfully, within a first range or a second range.

These and other objectives are attained with a vacuum system comprising a vacuum line, a pump, a pump motor, a pressure adjusting assembly, a pressure sensor and a system control means. Generally, the pump is connected to the vacuum line for drawing fluids therefrom, and the motor is connected to the pump to drive the pump. The pressure adjusting assembly is connected to the vacuum line for conducting fluid into that line at an adjustable rate. The pressure sensor is connected to the vacuum line to sense the pressure therein and to generate a pressure signal representing that pressure. The system control means is connected to the pressure sensor to receive the pressure signal therefrom and to generate a system control signal that is used to adjust the pressure in the vacuum line.

In the preferred operation of the vacuum system, the specific manner in which the pressure in the vacuum line is adjusted depends on the value of that pressure, and in particular, whether that pressure is in a first range or a second range. The control means determines whether the pressure in the vacuum line is in the first or second range. On the one hand, if the pressure in the vacuum line is in that first range, then the control signal from the control means is transmitted to the pressure adjusting assembly to adjust the pressure in the vacuum line by varying the amount of fluid conducted into that line via the pressure adjusting assembly. On the other hand, if the pressure in the vacuum line is within the second pressure range, then the control signal from the control means is transmitted to the pump motor to vary the speed of the pump and, thereby, the pressure in the vacuum line.

The vacuum system is well suited for use during ophthalmic surgery to aspirate the surgical site. In this use of the vacuum system, an aspiration tube is connected to the vacuum line; and the vacuum system is used, under the control of an operator, to produce a variable vacuum pressure in the aspiration tube, which is used to draw fluids and materials away from the surgical site.

Further benefits and advantages of the invention will become apparent from a consideration of the following detailed description given with reference to the accompanying drawings, which specify and show preferred embodiments of the invention.

DETAILED DESCRIPTION OF THE PREFERRED EMBODIMENTS

Figure 1:
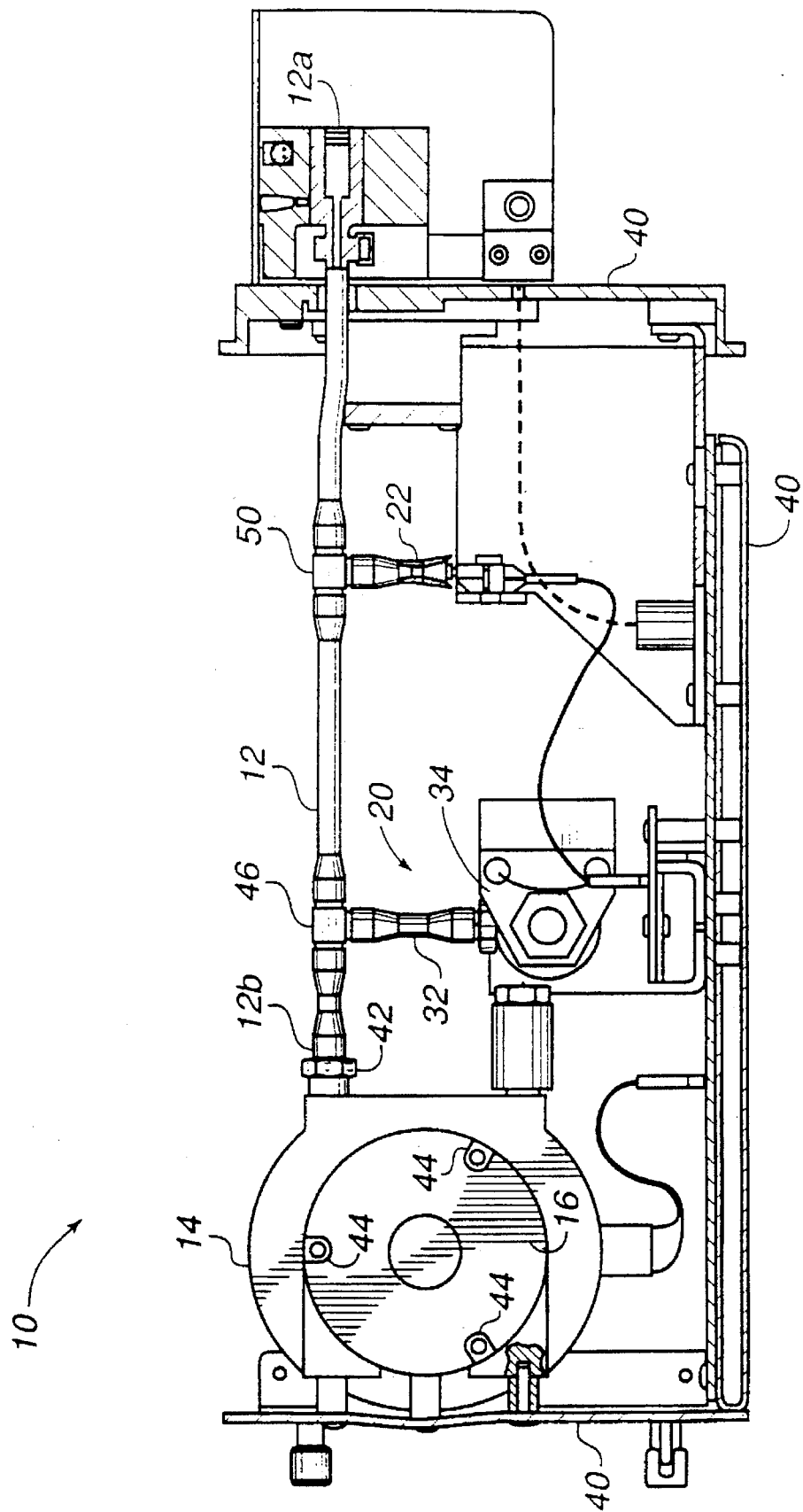
FIG. 1 is a side view of a vacuum system embodying the present invention.
Figure 2:
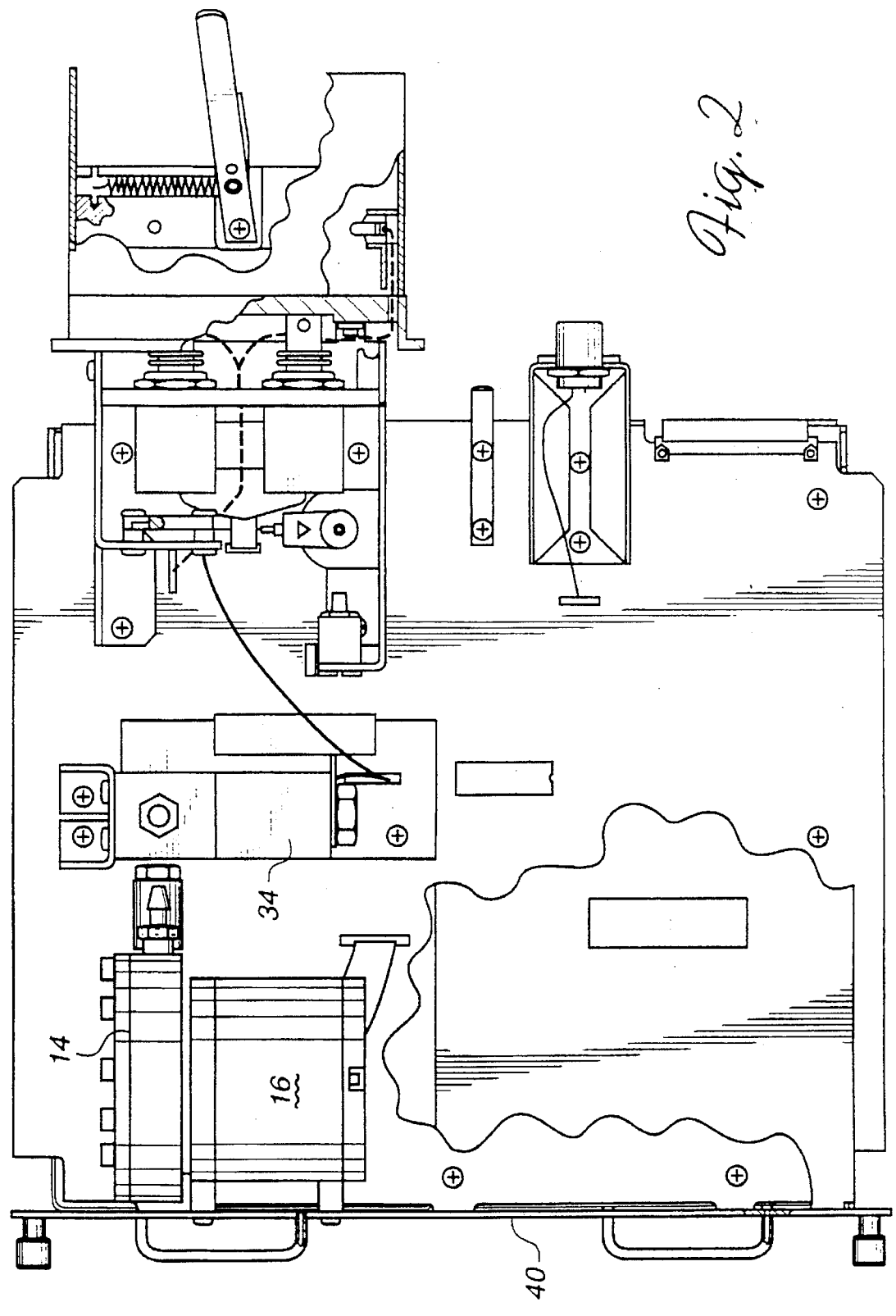
FIG. 2 is a top view of the vacuum system.
Figure 3:
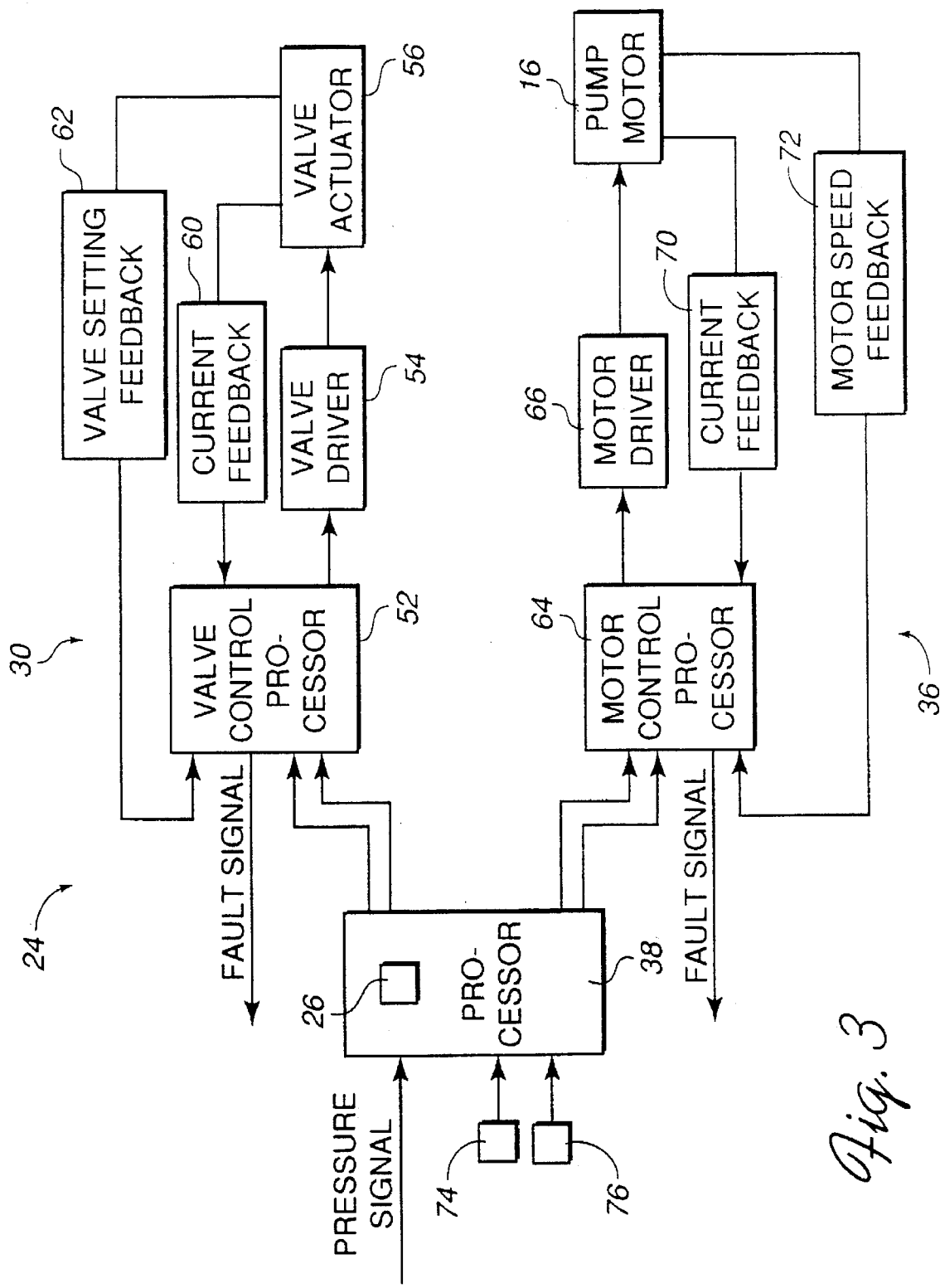
FIG. 3 is a schematic diagram of a control circuit of the vacuum system.

FIGS. 1, 2 and 3 illustrate vacuum system 10 generally comprising vacuum line 12, pump 14, pump motor 16, pressure adjusting assembly 20, pressure sensor 22 and system control means 24. Control means 24, in turn, includes signal generating means 26 and assembly control 30. Preferably, pressure adjusting assembly 20 includes fluid line 32 and valve 34, and system control means 34 further includes motor control 36. Also, with the embodiment of system 10 illustrated in the drawings, signal generating means 26 is part of processor 38, and the vacuum system further includes support structure 40.

Generally, pump 14 is connected to vacuum line 12 for drawing fluid therefrom, and motor 16 is connected to the pump to drive the pump. Pressure adjusting assembly 20 is connected to vacuum line 12 for conducting fluid into the vacuum line at an adjustable rate, and pressure sensor 22 is connected to the vacuum line to sense the pressure therein and to generate a pressure signal representing that pressure. System control means 24 is connected to pressure sensor 22 to receive the pressure signal therefrom. Signal generating means 26 generates a control signal representing the difference between the pressure in vacuum line 12 and a desired operating pressure, and assembly control 30 is provided to operate pressure adjusting assembly 20 selectively, in response to the signal from signal generating means 26, to vary the pressure in the vacuum line.

In the preferred operation of system 10, the specific manner in which the pressure in vacuum line 12 is adjusted depends on the value of that pressure, and in particular, whether that pressure is in a first range or a second range. In this operation of system 10, control means 24, specifically processor 38 thereof, determines whether the pressure in line 12 is in the first or second range. On the one hand, if the pressure in line 12 is in that first range, then the control signal from control means 24 is transmitted to pressure adjusting assembly 20, via assembly control means 26, to adjust the pressure in the vacuum line by varying the amount of fluid conducted into the vacuum line via the pressure adjusting assembly.

On the other hand, if the pressure in line 12 is in the second pressure range, then the control signal from control means 24 is transmitted to pump motor 16, via motor control 36, to vary the speed of pump 14 and, thereby, the pressure in the vacuum line. Also, preferably, when the pressure in vacuum line 12 is in the first pressure range, pump 14 is operated at a substantially constant speed; and when the pressure in vacuum line 12 is in the second pressure range, assembly 20, specifically valve 34 thereof, is closed to prevent fluid from entering the vacuum line via fluid line 32.

Processor 38 preferably determines whether the pressure in vacuum line 12 is within the above-mentioned first or second ranges by determining whether that pressure, as represented by the signal from pressure sensor 22, is above or below a set point value. If the pressure in vacuum line 12 is above that set point value, then the pressure in the vacuum line is considered to be in the first range; while if the pressure in vacuum line 12 is below that set point value, then the pressure in the vacuum line is considered to be in the second range.

More specifically, vacuum line 12 has inlet 12a and outlet 12b, and pump 14 is connect to the outlet of the vacuum line for drawing fluid therefrom and, in this way, reducing the pressure in the vacuum line. Vacuum line 12 may be connected to pump 14 in any appropriate manner, such as by means of fitting 42.

Preferably, pump 14 is a variable speed, variable capacity pump, and motor 16 is a variable speed motor. The speed of pump 14 may be adjusted to vary the rate at which fluid is withdrawn from vacuum line 12, and the speed of motor 16 is varied to adjust the speed of the pump. Motor 16 may be connected to pump in any suitable way. For instance, a plurality of bolts 44 may be used to mount motor 16 on pump 14; and a standard rotary transmission (not shown) may be used to transmit rotary motion from motor 16, specifically a motor shaft thereof, to pump 14, specifically a drive shaft thereof.

With the embodiment of pressure adjusting assembly 20 illustrated in the drawings, fluid line 32 includes an inlet and an outlet, and valve 34 is connected to the fluid line at or adjacent the inlet thereof. The inlet of fluid line 32 is in fluid communication with the ambient for receiving ambient air, the fluid line outlet is connected to and is in fluid communication with vacuum line 12 for conducting ambient air thereinto, and valve 34 is mounted on the fluid line to control the amount of ambient air conducted therethrough and thence into the vacuum line.

Preferably, valve 34 is an electrically operated proportional valve forming an opening or passageway having a size that can be varied or adjusted in a continuous manner over a given range, and the valve includes an actuator or motor that operates to vary the size of that opening or passageway, thereby to vary the amount of air conducted through fluid line 32 and into vacuum line 12. Valve 34 may be connected to line 32 in any appropriate manner, and line 32 may be connected to vacuum line 12 in any suitable way such as by means of T-fitting 46.

With the preferred embodiment of pressure sensor 22, a pressure transducer is connected to vacuum line 12, via T-fitting 50, so that a pressure equal to the pressure in the vacuum line is applied to the pressure transducer, and the transducer generates an electric signal having a voltage representing or proportional to the pressure in the vacuum line.

As discussed above, system control means 24 compares this pressure signal to a first value to determine if the pressure in vacuum line 12 is above or below a desired operating pressure; and if the actual pressure in vacuum line 12 is above or below that desired operating pressure, then signal generating means 26 generates an output signal representing the difference between the desired operating pressure and the actual pressure in the vacuum line. At the same time, system control means 24 also preferably compares the actual pressure in vacuum line 12 to a set point value to determine—if it is necessary to change the pressure in the vacuum line—how that pressure should be adjusted, either by adjusting valve 34 or by changing the speed of pump 14.

For example, the above-mentioned set point value may be a vacuum pressure of 100 mm. of mercury. To produce or to maintain a pressure in vacuum line 12 higher then 100 mm. of mercury—that is, between 0 and 100 mm. of mercury—pump 14 is operated at a constant speed, sufficient, in the absence of any effect of pressure adjusting assembly 20, to maintain a pressure of 100 mm. of mercury in the vacuum line, and valve 34 is operated to conduct sufficient ambient air into the vacuum line to raise the pressure therein to the desired value. To produce or to maintain a pressure in the vacuum line 12 less than 100 mm. of mercury—for example, between 100 and 500 mm. of mercury—valve 34 is closed and the speed of pump 14 is varied to adjust the pressure in the vacuum line to the desired value.

With the specific embodiment of control means 24 shown in the drawings, when processor 38 transmits the control signal to assembly control means 30, that signal is received by valve control processor 52. Processor 52 then transmits a signal to valve driver 54, which in turn transmits a signal to valve actuator 56 to operate valve 34 to increase or decrease the amount of fluid conducted through the valve and, in this way, to increase or decrease the pressure in vacuum line 12.

Preferably, in order to monitor the operation of valve actuator 56, means 60 and 62 are provided to sense current through the actuator and the valve position, and signals representing these parameters are transmitted back to valve control processor 52. Processor 52 preferably generates a valve fault signal in case the value of one of these sensed parameters moves outside a preferred range.

When processor 38 transmits the control signal to motor control means 36, that signal is received by motor control processor 64. Processor 64 then transmits a signal to motor driver 66, which in turn transmits a signal to pump motor 16 to operate pump 14 to increase or decrease the pressure in vacuum line 12. Preferably, in order to monitor the operation of pump motor 16, means 70 and 72 are provided to sense motor current and motor speed, and signals representing these parameters are transmitted back to motor control processor 64. Processor 64 preferably generates a motor fault signal in case the value of one of these sensed parameters moves outside a preferred range.

With the above-described arrangement, system control means 24 continues to produce a control signal—and the pressure in vacuum line 12 continues to be adjusted—until that pressure equals the desired operating pressure. When this happens, processor 38 stops producing the control signal. In addition, preferably means 74 and 76 are provided to allow an operator to adjust both the above-discussed desired operating pressure and set point pressure.

Preferably, pump 14, motor 16, vacuum line 12, T-fittings 46 and 50, valve 34 and transducer 22 are conventional, standard elements. Also, preferably pump 14 is a rotary vane pump and motor 16 is a variable speed DC motor. In addition, preferably pump 14 is capable of producing a vacuum pressure of 600 mm. of mercury in vacuum line 12. Under normal operating conditions, the lowest pressure maintained in vacuum line 12 is 500 mm. of mercury; however, pump 14 may be temporarily operated, for example at the start up of system 10, at maximum capacity, greater than 500 mm. of mercury, in order to reach more quickly a desired operating vacuum pressure in vacuum line 12.

System 10 may be used for a variety of purposes and in a variety of specific applications. For example, system 10 may be used during ophthalmic surgery to aspirate the surgical site. In this use of system 10, an aspiration tube (not shown) is connected to inlet 12a of vacuum line 12, and the vacuum system is used to produce a variable vacuum pressure in the aspiration tube, which is used to conduct fluids and materials away from the surgical site.

System 10 is very well suited for use in a modular console that includes a multitude of other modules for operating other instruments or for performing other tasks related to the ophthalmic procedure. For example, system 10 may be used in the console disclosed in copending application Ser. No. 08/330,920 pending (attorney docket 9369) filed herewith, the disclosure of which is herein incorporated by reference.

In such an application, processor 38 may be connected to a console processor that, generally, controls the overall operation of the console and that acts as a communications interface between the console and an operator. Also, commands to activate system 10, or components thereof, may be generated by the console processor and transmitted to processor 38. Likewise, data transmitted to or generated by processor 38 may be transmitted to the console processor to keep that processor, and the console operator, informed of that data.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

We claim:

1. A vacuum system comprising:

a vacuum line having an inlet and an outlet;

a pump connected to the outlet of the vacuum line for drawing fluid therefrom;

motor means connected to the pump to drive the pump;

a pressure adjusting assembly including a second fluid line forming a branch off said vacuum line having a second inlet for conducting fluid into the vacuum line at an adjustable rate to vary the pressure therein;

a pressure sensor connected to the vacuum line to sense the pressure therein and to generate a pressure signal representing the pressure in the vacuum line; and control means connected to the pressure sensor to receive the pressure signal therefrom, and including i) means to generate a control signal representing the differences between the pressure in the vacuum line and a desired pressure, ii) means to compare the pressure signal to a given value to determine whether the pressure in the vacuum line is above or below a set point value; and iii) means to direct the control signal to the pressure adjusting assembly if the pressure in the vacuum line is above the set point value, and to direct the control signal to the motor means if the pressure in the vacuum line is below the set point value.

2. A vacuum system according to claim 1, wherein:

the pump is a variable speed rotary vane pump for varying the pressure in the vacuum line; and the motor means is a variable speed motor for driving the pump at a variable speed; and the control means further includes means to conduct the control signal to the motor means to vary the speed thereof and of the pump to adjust the pressure in the vacuum line.

3. A vacuum system according to claim 1, wherein the control means further includes means to adjust the set point value.

4. A vacuum system according to claim 1, wherein:

the pressure adjusting assembly includes i) said second fluid line in communication with the vacuum line for conducting ambient air thereinto to increase the pressure in the vacuum line, and ii) a valve connected to the fluid line and controlling the amount of ambient air conducted therethrough and into the vacuum line; and when the pressure in the vacuum line is below said set point value, the valve is closed to prevent air from passing from the fluid line into the vacuum line.

5. A vacuum system according to claim 1, wherein:

the pressure adjusting assembly includes i) said second fluid line in fluid communication with the ambient and with the vacuum line for conducting ambient air thereinto to increase the pressure in the vacuum line, and ii) an electrically operated proportional valve connected to the fluid line and controlling the amount of ambient air conducted therethrough and into the vacuum line, said valve being adjustable for conducting fluid into the vacuum line at an adjustable rate; and the control signal is an electrical signal and is conducted to the proportional valve to adjust the valve and the rate at which ambient air is conducted through the fluid line and into the vacuum line.

6. A vacuum system for ophthalmic surgery, comprising:

a vacuum line having first and second inlets and an outlet;

a pump coupled to the outlet of the vacuum line for drawing fluid therefrom;

a motor coupled to the pump to drive the pump;

a sensor for sensing at least one parameter of operation of the vacuum system;

a valve having an inlet for admitting air, an outlet coupled to the second vacuum line inlet, an orifice of variable size, variable open positions to admit variable amounts of air from the valve inlet, through the valve orifice to the second vacuum line inlet, and a closed position to prevent the admission of air from the valve inlet through the valve to the vacuum line second inlet;

a comparator for comparing a sensed parameter of operation to a predetermined set point value;

a valve controller for varying the size of the valve orifice to vary the pressure in the vacuum line if the sensed parameter of operation is above the predetermined set point value and for closing the valve if the sensed parameter of operation is below the predetermined set point value; and a motor controller for varying the motor speed to vary the pressure in the vacuum line when the sensed parameter of operation is below the predetermined set point value.

7. The vacuum system of claim 6 wherein the pump is a rotary vane pump and the sensor includes a pressure sensor for sensing the pressure of the vacuum line and for generating at least one signal including a pressure signal representing the sensed vacuum pressure in the vacuum line, wherein the motor controller has a first input for a desired pressure signal representing a desired vacuum line pressure and a second input coupled to the pressure sensor for controlling the motor speed as a function of the difference between the vacuum line pressure sensed by the pressure sensor and the desired vacuum line vacuum pressure when the sensed parameter of operation is below the predetermined set point value.

* * * * *